United States Patent [19]

Wakamatsu et al.

[11] Patent Number: 4,940,730

[45] Date of Patent: Jul. 10, 1990

[54] ANGIOGENESIS ENHANCER

[75] Inventors: Kaori Wakamatsu, Tsukuba; Koichi Kondo, Sohraku; Katsuichi Sudo, Takatsuki, all of Japan

[73] Assignee: Takeda Chemical Industries, Ltd., Osaka, Japan

[21] Appl. No.: 253,060

[22] Filed: Oct. 3, 1988

[30] Foreign Application Priority Data

Oct. 29, 1987 [JP] Japan .................. 62-274461
Jul. 7, 1988 [JP] Japan .................. 63-169763

[51] Int. Cl.$^5$ .................. A61K 31/16; A61K 31/20
[52] U.S. Cl. .................. 514/560; 514/625; 514/627
[58] Field of Search .................. 514/625, 627, 560

[56] References Cited

U.S. PATENT DOCUMENTS 3,219,659 11/1965 Skau et al. .................. 260/239

FOREIGN PATENT DOCUMENTS

WO86/01111 2/1986 PCT Int'l Appl. .

OTHER PUBLICATIONS

J. Folkman, Angiogenesis, Initiation and Control 212:1982, Annals New York Academy of Sciences.
D. Form, et al., PGE$_2$ and Angiogenesis[1] (41548), Proceedings of the Society for Experimental Biology and Medicine 172,214–218 (1983).
R. Crum, et al., A New Class of Steroids Inhibits Angiogenesis in the Presence of Heparin or a Heparin Fragment, Science vol. 230, 1375–1378 (1985).
R. Mod, et al., The Plasticizing Characteristics of Some N,N-Dimethylamides and Ester-Amides of Long--Chian Fatty Acids, The Journal of The American Oil Chemists' Society, vol. 45:385–387.

Primary Examiner—Stanley J. Friedman
Attorney, Agent, or Firm—David G. Conlin; Gregory D. Williams; Patricia A. McDaniels

[57] ABSTRACT

The present invention relates to a composition with enhanced angiogenic activity which contains a compound of the formula:

R—A wherein R stands for a higher aliphatic hydrocarbon residue, and A stands for hydrogen atom, carboxyl group, hydroxyl group, carbamoyl group which may be substituted or amino group which may be substituted or quaternized.

The composition of the present invention has been found to enhance blood vessel formation, which is useful for the treatment of various ischemic diseases, trauma, thermal burns, alopecia, etc.

4 Claims, No Drawings

ANGIOGENESIS ENHANCER

This invention relates to a composition with enhanced angiogenic activity.

Angiogenesis is an important biological phenomena in mammals, involving, for example, in the processes such as embryological development, wound healing, and inflammation.

More specifically, when tissue and organs differentiate in embryological development, transmission of information and the carrying of oxygen, carbon dioxide, nutrients, waste materials, etc. become necessary, which in turn require the formation of new blood vessels.

Angiogenesis is caused by angiogenic factors and has three fundamental stages, i.e. degradation of endothelium matrix, migration of endothelial cells (blasting of cells) and proliferation of endothelial cells (elongation of capillary tube).

Angiogenic factors are considered to be anaerobic cell-metabolites and have been in a number of places in mammals including observed at the hypoxic site in cancerous tissue or wound healing tissues. It is believed that these factors are also present in blood components as leakage of the blood components induces angiogenesis.

Angiogenic subtances which have been reported include fibroblast growth factor (FGF), epidermal growth factor (EGF), angiogenin, etc. [Ann. NY Acad. Sci., 401, 212 to 227 (1982)]. Eicosanoids such as leukotrienes, prostaglandins have also been reported to possess angiogenic activity [Proc. Soc. Exp. Biol. Med., 172, 214 to 218 (1983)].

Furthermore, Catsimpoolas et al. found an angiogenic factor by extracting lipid fractions from omenta of cats [See, for example, WO-8601111-A]. In that reference, the lipid fractions of the omenta, containing atoms of oxygen, hydrogen and carbon and having a dalton range of 150 to 1100, are considered possessing angiogenic activity. It was further reported with explanation that hydrocarbons, in which the number of carbon atoms of the lipid does not exceed 20, were included. That group subsequently reported that gangliosides were found in the lipid fractions derived from omentum and these compounds possessed angiogenic activity [See, for example, WO87/01939].

The present inventors have an interest in characteristic pharmacological actions of substances capable of enhancing angiogenesis, and have conducted an extensive search for compounds which can actually be provided as pharmaceutical preparations, etc., and as a result have found that certain types of fatty acid derivatives possess a strong activity of enhancing angiogenesis. Based on these findings, the present inventors synthesized higher aliphatic hydrocarbon compounds and conducted pharmacological studies on those compounds, and accomplished the present invention.

The present invention provides a composition with enhanced angiogenic activity comprising a compound represented by the formula:

$$R—A \qquad (I)$$

wherein R stands for a higher aliphatic hydrocarbon residue, and wherein any double bond present in a hydrocarbon residue may be glycolated or epoxidated, and A stands for a hydrogen atom, carboxyl group, hydroxyl group, carbamoyl group which may be substituted or amino group which may be substituted or quaternized.

The higher aliphatic hydrocarbon residues, represented by R include saturated or unsaturated higher aliphatic hydrocarbon groups, which may be a straight-chain or branched chain.

For unsaturated higher aliphatic hydrocarbon residue, the unsaturated bond is preferably a double bond, which may take the form of di-, tri-, tetra-substitution, and may take either configuration of cis- or trans-.

When multiple unsaturated bonds exist, the mode of substitution and configuration may be a combination of the above-mentioned ones or of the single mode. And, these unsaturated bonds may be independent or conjugated.

The carbon number of the higher aliphatic hydrocarbon residue is preferably in a range of from 14 to 30, most preferably from 16 to 26. Those of natural types and having an even number of carbon atoms are especially preferred.

For higher aliphatic hydrocarbon residues having unsaturated bonds, the number of double bonds is preferably 1 to 8, most preferably 1 to 5 with the double bonds being independent.

One or two or more of those double bonds may be glycolated and/or epoxidated. In the case of glycol, the adjacent two hydroxyl groups may be either threo- or erythro-configuration.

Where A is a substituted carbonyl, the substituents include, for example, lower($C_{1-6}$)alkyl, lower cyclo($C_{3-6}$) alkyl, phenyl, phenyl-$C_{1-3}$alkyl, hydroxyl, etc. The lower alkyl, phenyl, phenyl-$C_{1-3}$alkyl may be substituted with hydroxyl group, $C_{1-3}$alkoxy, carboxyl, halogen (e.g. fluorine, bromine, chlorine, iodine), etc. The carbamoyl group is mono- or di-substituted one, and, further, may form a 5-to 6-membered nitrogen-containing heterocyclic ring (e.g. piperidine, pyrrolidine, thiazolidine, thiazine, morpholine, etc.) together with the nitrogen atom of the carbamoyl group. The nitrogen-containing heterocyclic ring groups may further substituted by a heterocyclic group such as pyridine, carboxyl, a lower($C_{1-3}$)alkoxy carbonyl, etc.

When A is a substituted amino group, the substituents are exemplified by a lower($C_{1-3}$)alkyl, a lower cyclo($C_{1-3}$)alkyl, phenyl, phenyl-$C_{1-3}$alkyl, etc., including both mono- and di-substituted amines. Where the amino group is quaternized, examples of quaternary amine include those formed by addition of hydrogen halogenide, a lower ($C_{1-3}$)alkyl-halogen, etc. to the disubstituted amine. A primary amine or trimethyl ammonium is preferable.

The preferred compounds employed in the present invention include a higher fatty acid and the corresponding optionally substituted amide.

The above-mentioned higher fatty acid and higher fatty acid amide are exemplified as follows. In parenthesis, the number of carbon atoms, number of double bonds and position(s) of double bonds are noted in the order mentioned:

myristic acid (14:0), palmitic acid (16:0), stearic acid (18:0), arachidic acid (20:0), behenic acid (22:0), lignoceric acid (24:0), cerotic acid (26:0), elaidic acid (18:1, $\Delta 9$), linoleic acid (18:2, $\Delta 9$, 12), arachidonic acid (20:4, $\Delta 5$, 8, 11, 14), erucic acid (22:1, $\Delta 13$ cis), brassidic acid (22:1, $\Delta 13$ trans), docosahexaenoic acid (22:6, $\Delta 4$, 7, 10, 13, 16, 19), nervonic acid (24:1, $\Delta 15$) and their amides optionally having the above-mentioned substituents.

Above all, behenic acid, erucic acid, brasidic acid and their amides are employed advantageously, and such preferable compounds can be shown by the general formula (II).

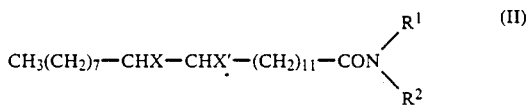

wherein X and X' each stand for hydrogen atom or hydroxyl group, or X and X', taken together, form an ether linkage or a bond; $R^1$ and $R^2$ independently stand for hydrogen atom, hydroxyl group, lower alkyl or phenyl group which may be substituted, or form a heterocyclic group together with the adjacent nitrogen atom, provided that $R^1$ and $R^2$ are not hydroxyl group simultaneously. As the above $R^1$ and $R^2$, mention is made of the substituent shown as those of carbamoyl of (I).

Compounds represented by the general formula (III) included in the compound (II) are novel compounds which have never been disclosed in literature references.

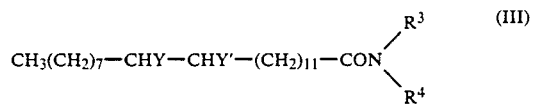

where Y and Y' each stand for hydroxyl group, or, taken together, bond; either one of $R^3$ and $R^4$ stands for hydrogen atom, and the other stands for lower alkyl or phenyl group which may be substituted or, taken together with the adjacent nitrogen atom, forms pyrrolidine or thiazine ring which may be substituted.

The compounds of formula (I) can be derived from an animal, or prepared as hydrolyzates thereof. There are also producible by means of synthetic chemistry or enzymatic chemistry, or they are producible by chemical synthesis.

Production of fatty acid amide from fatty acid, for example, comprises converting fatty acid to fatty acid chloride by conventional means, followed by addition of corresponding amine or ammonia to afford the fatty acid amide.

By subjecting a lower($C_{1-3}$)alkyl ester or amide of fatty acid to reduction using a metallic hydride such as lithium aluminium hydride or the like, the corresponding alcohol or amine can be produced, respectively.

Furthermore, by subjecting an alcohol corresponding to the fatty acid obtained as above to halogenation with a mineral acid e.g. hydrobromic acid, then by allowing the halogenated product to react with a tertiary amine, a quaternized ammonium salt of higher aliphatic hydrocarbon can be obtained.

Epoxidation can be conducted by allowing a compound of formula (I) having a double bond to react with an epoxidizing agent e.g. m-chloroperbenzoic acid. Glycolation can be conducted by subjecting a compound having a double bond to oxidation by the use of osmium tetraoxide, when desired, in the presence of an oxidizing agent e.g. hydrogen peroxide, tertiary butyl hydroperoxide or the like.

Thus-obtained compound of formula (I) can be purified and isolated by a conventional means including extraction, chromatography, recrystallization or the like, when desired.

The compounds of formula (I) employed in the present invention possess a strong angiogenic activity and their toxicity is relatively low. Therefore, they can be used for the therapy or amelioration of various ischemic diseases, trauma, thermal burns, alopecia, etc. in mammals (monkey, dog, cat, man, etc.).

In ischemic diseases such as myocardial infarction, the compound of formula (I) serves to stimulate the angiogenesis or its induction in the myocardial tissue to enhance blood circulation.

In trauma or thermal burns, the compound of formula (I) serves to prevent the loss of body fluid or infections and to form new blood vessels at the wound to quicken the cure.

In alopecia, the compound of formula (I) enhances the formation of blood vessels and satisfies the supplement of oxygen and nutrients to perform local hair-growing.

The compounds of formula (I) are relatively low in toxicity and they can be administered orally or non-orally.

For example, for the therapy of ischemic diseases, the compounds (I) are usually administered in the form of tablets or capsules or by injections. In this case, the dosage per adult per day is about 10 to 500 mg.

For the therapy or amelioration of trauma, thermal burns and alopecia, the compounds (I) are applied to the site concerned 1 to 4 times per day as usually a solution of a concentration of about 0.1 to 5% (W/V) or as an ointment of about 1 to 10% (W/W).

The compounds (I) of the present invention are of a relatively low molecular weight and can be produced easily as highly pure and stable compounds. These compounds can be formulated into various pharmaceutical preparations with physiologically acceptable carriers, excipients, diluents, etc.

EXPERIMENTAL EXAMPLE 1 (CAM ASSAY)

CAM (Chorio Allantoic Membrane) assay was conducted on various compounds of the present invention. The technique of the CAM assay was that modified somewhat on Auerbach's method [Developmental Biology, 41, 391 (1974)]. More specifically, hen's fertile eggs were incubated for three days at 37° C. (Napco carbon dioxide incubator-6300 was employed, $CO_2$:0% $H_2O$ saturated). Polypropylene-made discs (6 mm. diameter) were spotted with a chloroform:ethanol (1:4 by volume) solution of each compound so that the concentration may be 0, 0.25, 0.64, 1.6, 4, 10 and 25 ug, respectively. The test materials were air-dried in a clean bench, which were then placed quietly on hen's chlorioallantoic membrane, followed by incubation at 37° C. for further three days. Then, the vascularization state was observed. The results obtained were shown in Table 1 and Table 2. In the tables, the positive rates were calculated on the following basis. Namely, degrees of neovascularization were determined as + + for very strong, + for strong, ° for weak and — for negative, and they were numerized as 10, 7, 3 and 0, respectively. The average numerical value in each of the concentrations of the respective samples was made as positive rate. Further, the amount of the drug which gave the numerical value 5 in each sample was shown as $ED_{50}$ value (ug/disc).

TABLE 1

| Compound | Amount of Sample (μg) Positive rate of CAM assay | | | | | | |
|---|---|---|---|---|---|---|---|
| | 25 | 10 | 4 | 1.6 | 0.64 | 0.00 | $ED_{50}$ |
| Acid amide compound | | | | | | | |
| Butyramide (4:0) | 0 | 0 | 0 | 0 | 0 | — | — |
| Lauramide (12:0) | 0.3 | 0 | 0 | 0.7 | 0.3 | — | — |
| Myristamide (14:0) | 3.5 | 2.6 | 1.3 | 0 | 0 | — | — |
| Palmitamide (16:0) | 7.7 | 2.4 | 0.3 | 0 | 0 | — | 15.6 |
| Stearamide (18:0) | 6.9 | 7.7 | 7.6 | 2 | 0 | 0 | 2.63 |
| Arachidamide (20:0) | 7.4 | 4.6 | 3.4 | 2.8 | 0 | — | 11.5 |
| Behenamide (22:0) | 10 | 10 | 7.6 | 1.8 | 0 | 0 | 2.76 |
| Oleamide (18:1,$\Delta^9$) | 6.8 | 7.8 | 0 | 0.6 | 0 | — | 16.7 |
| Arachidonamide (20:4, $\Delta^{5,8,11,14}$) | 9.6 | 7.4 | 2.9 | 1.6 | 1.3 | — | 6.13 |
| Erucamide (22:1,$\Delta^{13}$) | 10 | 10 | 9.4 | 3.4 | 1.4 | 0 | 2.13 |
| Brassidamide (22:1,$\Delta^{13}$trans) | 10 | 9.3 | 7.4 | 2.0 | 0 | — | 1.89 |
| Erucamide Derivs. | | | | | | | |
| N-methyl | 10 | 10 | 7.8 | 2.3 | 0.8 | 0 | 2.90 |
| N,N-dimethyl | 9.3 | 8.5 | 3.3 | 1.5 | 0 | — | 5.41 |
| piperidine | 8.5 | 7.0 | 4.3 | 2.1 | 0.4 | 0 | 4.93 |
| morpholine | 10 | 8.5 | 5.8 | 3.0 | 1.5 | 0 | 3.17 |
| N, N-di-diethanol | 10 | 10 | 8.0 | 2.3 | 1.0 | 0 | 2.42 |
| proline methylester | 10 | 7.8 | 5.0 | 2.3 | 0.8 | 0 | 4.00 |
| m-aminobenzoic acid | 10 | 10 | 7.4 | 6.0 | 2.0 | 0 | 1.28 |
| 2-Py-Thia-CO$_2$H | 10 | 10 | 6.8 | 2.6 | 2.8 | 0 | 2.67 |
| carboxymethyl amine | 10 | 7.0 | 2.6 | 0 | 0 | — | 6.58 |
| 2-NH$_2$-4-Cl-BzCO$_2$H | 10 | 8.0 | 5.6 | 4.2 | 2.6 | 0 | 2.70 |
| carboxyamine | 10 | 9.3 | 7.0 | 1.5 | 0.8 | 0 | 3.17 |
| Erucamide, diOH (22:0, 13,14-cisOH) | 9.4 | 7.0 | 3.8 | 2.0 | 0 | — | 5.62 |
| 13,14-Epoxyerucamide (22:0) | 10 | 10 | 8.5 | 3.3 | 1.5 | 0 | 2.22 |

—: not measured
2-Py-Thia-CO$_2$H: 4-carboxy-2-(4-pyridyl)thiazoline
Bz: benzyl

TABLE 2

| Compound | Amount of Sample (μg) Positive rate of CAM assay | | | | | | |
|---|---|---|---|---|---|---|---|
| | 25 | 10 | 4 | 1.6 | 0.64 | 0.00 | $ED_{50}$ |
| Fatty acid | | | | | | | |
| Oleic acid (18:1,$\Delta^9_{cis}$) | 7 | 4 | 2.5 | 0.8 | 0 | 0 | 13.7 |
| Elaidic acid (18:1,$\Delta^9_{trans}$) | 4 | 4 | 3 | 0 | 0 | 0 | — |
| Linoleic acid (18:2,$\Delta^{9,12}$) | 10 | 6 | 2.5 | 1.8 | 0 | 0 | 7.69 |
| Arachidonic acid (20:4, $\Delta^{5,8,11,14}$) | 10 | 7 | 5.3 | 3.5 | 2.5 | 0 | 3.64 |
| Erucic acid (22:1,$\Delta^{13}$ $_{cis}$) | 9.4 | 8.2 | 4 | 2.8 | 1.4 | 0 | 4.69 |
| Brassidic acid (22:1,$\Delta^{13}$ $_{trans}$) | 10 | 9.3 | 6 | 6 | 3.5 | 0 | 1.82 |
| Docosahexaenoic acid(22:6, $\Delta^{4,7,10,13,16,19}$) | 4.8 | 0.6 | 0 | 0 | 0 | 0 | — |
| Lignoceric acid (24:0) | 6.2 | 7.6 | 4.6 | 2 | 1.4 | 0 | 4.61 |
| Nervonic acid (24:1,$\Delta^{15}$) | 8.5 | 9.3 | 7.8 | 2.5 | 1.8 | 0 | 2.75 |
| Cerotic acid (26:0) | 8.5 | 9.3 | 7.8 | 2.5 | 1.8 | 0 | 2.75 |
| Myristic acid (14:0) | 5 | 4 | 0.8 | 0 | 0 | 0 | 25.0 |
| Palmitic acid (16:0) | 7.6 | 3.2 | 0 | 0 | 0 | 0 | 14.5 |
| Stearic acid (18:0) | 9.4 | 6.8 | 1.8 | 0 | 0 | 0 | 7.14 |
| Ricinoleic acid (18:1,$\Delta^9_{cis}$,12OH) | 3.2 | 2.6 | 1.2 | 1.8 | 0 | 0 | — |
| Arachidic acid (20:0) | 8.8 | 7.6 | 4.6 | 4.6 | 0 | 0 | 4.00 |
| Erucic acid diOH (22:0, 13, 14-cisOH) | 10 | 8.2 | 7.4 | 2.0 | 0 | 0 | 3.45 |
| Others | | | | | | | |
| 13-Docosen-1-ol (22:1,$\Delta^{13}_{cis}$) | 10 | 9.4 | 6.8 | 4.8 | 1.4 | 0 | 2.15 |
| 13, 14-Eopxy-docosan-1-ol (22:0) | 10 | 9.3 | 3.3 | 0 | 0 | 0 | 5.18 |
| 1-Amino-13-docosene·HCl (22:1,$\Delta^{13}_{cis}$) | >10 | 10 | 8.8 | 7.0 | 3.4 | 0 | 0.94 |
| Docosan-1-ol (22:0) | 10 | 10 | 8.3 | 1.8 | 0 | 0 | 2.55 |
| 1-Trimethyammonio docosane bromide (22:0) | — | 8.0 | 5.0 | 4.5 | 0 | 0 | 4.00 |
| 1-Docosene (22:1,$\Delta^1$) | 9.3 | 10 | 2.5 | 0 | 0 | 0 | 5.46 |

—: not measured

EXPERIMENTAL EXAMPLE 2 (RAT CORNEA TEST)

The experiment was conducted by modifying the method of Gimbrone et al. [J. National Cancer Institute, 52 (2), 413 (1974)]. Namely, Wister rats (14-week old, male) were anesthetized, then pockets (about 2×3 mm in size) were provided in the cornea. A gel of each test compound enveloped in ethylene-vinyl-acetate copolymer (Elvax ®-40) was prepared, which was transferred into the pocket, and the state of elongation of blood vessels after two weeks was observed. The test samples enveloped were erucamide, lauramide and erucic acid, and, as the control, Elvax ®-40 in which nothing was enveloped was used. The results are shown in Table 3. As with the result of the CAM assay in Experimental Example 1, a strong elongation action was observed in erucamide and erucic acid.

TABLE 3

Results of Rat Cornea Test

| Compound | Amount of test material | Action of elongation of blood vessel |
|---|---|---|
| Erucamide | 30 μg | + + |
| Erucic acid | 30 μg | + + |
| Lauramide | 60 μg | — |
| Carrier (only Elvax ®-40) | 0 | — |

+, + +: blood vessel elongation action positive
—: blood vessel elongation action negative

EXPERIMENTAL EXAMPLE 3 (MOUSE DORSAL AIR-SACK METHOD)

Experimental work was conducted in accordance with the method of Yoshii et al. [Igaku no ayumi, 122 (No. 10), p. 890 (1982)]. More specifically, ICR mice (9-week old, males) were anesthetized, and the hair at the dorsal site was shaved with clippers. The site was sterilized with alcohol, and an injection needle was inserted at the site located at a distance of 1 cm from the tail side. Through the needle, about 20 ml of air was introduced. Then, the air in the air-sack (on the tail side) was drawn out. Test samples enveloped in Elvax ®-40 were inserted into both, left and right, sides (at one of the both sides, only Elvax ®-40 as the control). The incised site was closed, and, ten days later, the site was incised again and the state of elongation of blood vessel was observed. The test samples enveloped were erucamide, lauramide and erucic acid, and the results compared with one another. As shown in Table 4, a strong action of blood vessel elongation was observed in erucamide, similar to the results of CAM assay in Experimental Example 1.

TABLE 4

Results obtained by mouse dorsal air-sack method

| Compound | Amount of test sample | Blood elongation action |
|---|---|---|
| Erucamide | 1 mg | + + |
| Lauramide | 1 mg | − |

+, + +; blood vessel elongation action positive
−: blood vessel elongation action negative

EXAMPLES

Example 1 (Tablet)

Erucamide: 100 mg
Cornstarch: 90 mg
Lactose: 25 mg
Hydroxypropyl cellulose L: 25 mg
Total: 240 mg (per tablet)

To erucamide are added cornstarch, lactose and hydroxypropyl cellulose, and the mixture is granulated, followed by tableting.

Dosage : 1 to 3 tablets/adult/day, after each meal.

Example 2 (Ointment)

Erucamide: 1 g
Polyethylene glycol: 50 g
Ethylene glycol: 40 g
Purified water: 10 g are sufficiently blended to give a paste, which is filled into a wide-mouthed bottle, and the ointment thus obtained is applied to the affected part 3 to 4 times a day.

Example 3 (Ointment)

Erucamide: 1 g
White vaseline: 50 g are blended to give a paste, which is filled into a tube, and the ointment thus obtained is applied to the affected part 3 to 4 times a day.

Example 4 (Liquid medicine)

Erucamide: 1 g
Tween 80: 0.5 g
Ethanol: 20 ml
Purified water: 80 ml are blended to give a solution, which is applied to the affected part 3 to 4 times a day.

Example 5

(i) Synthesis of N-erucoyl-proline methyl ester

In methylene chloride (10 ml) was dissolved erucic acid (2 g). To the solution was added dropwise oxalyl chloride (1.1 ml), and the mixture was refluxed for one hour under heating, followed by concentration to give acid chloride. The acid chloride was stirred, together with L-proline methyl ester (980 mg), in THF (15 ml)-water (1 ml) in the presence of $NaHCO_3$ (800 mg) at room temperature for 15 hours. The solvent was concentrated. To the residue was then added water, and the mixture was subjected to extraction with methylene chloride. The extract was dried and concentrated, followed by purification by means of a silica gel column chromatography (hexane:ethyl acetate=3:1) to obtain a colorless oily product [1.09 g (yield 41%)].

oil. $^1$H-NMR ($CDCl_3$) δ: 0.7 to 1.0 (3 H, m), 1.2 to 2.5 (40 H, m), 3.4 to 3.7 (2H, m), 3.69 (3H, s), 4.3 to 4.6 (1 H, m), 5.2 to 5.5 (2 H, m)

(ii) Synthesis of N-methyl erucamide

In a manner similar to (i), erucic acid (3.39 g) was converted to its acid chloride, to which was added a 40% aqueous solution of methylamine. The mixture was stirred for 30 minutes under ice-cooling. The reaction mixture was subjected to extraction with isopropyl ether. The extract was dried and concentrated. The concentrate was recrystallized from hexane to afford pale orange crystals [1.80 g (yield 51%)], m.p. 48 to 49° C.

$^1$H-NMR ($CDCl_3$) δ: 0.7 to 1.0 (3 H, m), 1.1 to 2.3 (36 H, m), 2.78 (3 H, d, J=5 Hz), 5.33 (2 H, t, J=5 Hz), 5.3 to 5.8 (1 H, brs)

(iii) Synthesis of N-ercoyl-3-aminobenzoic acid

In a manner similar to (i), erucic acid (1 g) was converted to its acid chloride, to which was added 3-aminobenzoic acid (403 mg). The mixture was stirred in methylene chloride in the presence of pyridine at room temperature for three hours. The solvent was concentrated, then the residue was washed with water, ether and methanol, then dried, followed by recrystallization from ethanol to afford colorless crystals [1.18 g (yield 88%)], m.p. 171 to 174° C.

$^1$H-NMR ($d_6$-DMSO) δ: 0.71 to 1.0 (1 H, m), 1.1 to 2.5 (36 H, m), 5.2 to 5.5 (2 H, m), 7.2 to 7.7 (2 H, m), 7.8 to 8.0 (1 H, m), 8.22 (1 H, brs), 9.95 (1 H, brs)

(iv) Synthesis of N-erucoyl-2-(4-pyridinyl)-4-thiazoline carboxylic acid

In a manner similar to (i), erucic acid (1 g) was converted to its chloride, to which was added 2-(4-pyridinyl)-4-thiazolidine carboxylic acid (618 mg). The mixture was stirred in pyridine (6 ml)-methylene chloride (2 ml) at room temperature for two hours. The solvent was concentrated, then the residue was washed with water. Resultant precipitates were dried and purified by means of a silica gel column chromatography (chloroform:methanol=10:1), followed by recrystallization from methanol to afford colorless crystals [1.58 g (yield 99%)], m.p. 156 to 158° C.

$^1$H-NMR ($CDCl_3$—$CD_3OD$) δ: 0.5 to 2.6 (39 H, m), 3.3 to 3.7 (2 H, m), 5.1 to 5.5 (3 H, m), 6.25 (1 H, brs), 7.2 to 7.4 (2 H, m), 8.4 to 8.7 (2 H, m)

(v) Synthesis of N-erucoyl glycinamide

In a manner similar to (i), erucic acid (2.12 g) was converted to its acid chloride, to which was added glycine amide hydrochloride (692 mg). The mixture was stirred in THF (5 ml)-water (3 ml) in the presence of potassium carbonate (2 g) at room temperature for three hours. The solvent was concentrated, and the residue was washed with water and methylene chloride. Resulting precipitates were air-dried, followed by recrystallization from ethanol to afford colorless crystals [1.08 g (yield 44%)], m.p. 128 to 130° C.

$^1$H-NMR ($d_6$-DMSO) δ: 0.7 to 1.0 (3 H, m), 1.0 to 1.6 (30 H, m), 1.7 to 2.2 (6 H, m), 3.57 (2 H, d, J=6 Hz), 5.2 to 5.4 (2 H, m), 6.90 (1 H, brs), 7.18 (1 H, brs), 7.85 (1 H, brs)

(vi) Synthesis of N-erucoyl-2-amino-5-chlorobenzoic acid

In a manner similar to (i), erucic acid (1.05 g) was converted to its acid chloride, to which was added 2-amino-5-chlorobenzoic acid (530 mg). The mixture was stirred in pyridine (5 ml)-methylene chloride (2 ml) at room temperature for three hours. The solvent was concentrated and the residue was washed with 0.5N HCl and methanol. Resulting precipitates were dried, followed by recrystallization from ethanol to afford pale yellow crystals [550 mg (36%)], m.p. 159 to 162° C.

$^1$H-NMR (CDCl$_3$) δ: 0.7 to 1.0 (3 H, m), 1.2 to 2.6 (36 H, m), 5.2 to 5.5 (2H, m), 7.50 (1 H, dd, J=9.3 Hz), 8.08 (1 H, d, J=3 Hz), 8.73 (1 H, d, J=9 Hz), 9.93 (1 H, brs), 11.4 (1 H, brs)

(vii) Synthesis of 13,14-dihydroxydocosanamide

To an acetone (150 ml) solution consisting of erucamide (2 g), tetraethyl ammonium acetate (250 mg) and a 70% aqueous solution (1.3 ml) of t-BuOOH was added a 0.5% t-BuOH solution (0.5 ml) of osmium tetraoxide. The mixture was stirred at room temperature for five days. To the reaction mixture was added a 10% solution of sodium hydrogensulfite (30 ml), and the mixture was stirred for 30 minutes. The reaction mixture was subjected to filtration to collect crystals, then the crystals were washed with acetone, followed by drying to afford colorless crystals [728 mg (yield 33%)], m.p. 153 to 154° C.

$^1$H-NMR (CDCl$_3$—CD$_3$OD) 67 : 0.8 to 1.0 (3 H, m), 1.1 to 1.9 (34 H, m), 2.1 to 2.4 (2 H, m), 3.3 to 3.6 (2 H, m)

What is claimed is:

1. [The] A composition [according to claim 10, wherein] with enhanced angiogenic activity which contains an effective amount of the compound [is] erucamide[.], together with a physiologically acceptable carrier, excipient, or diluent therefor.

2. [The] A composition [according to claim 10, wherein] with enhanced angiogenic activity which contains an effective amount of the compound [is] N-erucoyl-3-aminobenzoic acid[.], together with a physiologically acceptable carrier, excipeint, or diluent therefor.

3. A composition with enhanced angiogenic activity which contains an effective amount of the compound erucic acid, together with a physiologically acceptable carrier, excipient, or diluent therefor.

4. A composition with enhanced angiogenic activity which contains an effective amount of the compound brassidamide, together with a physiologically acceptable carrier, excipient, or diluent therefor.

* * * * *

UNITED STATES PATENT AND TRADEMARK OFFICE
CERTIFICATE OF CORRECTION

PATENT NO. : 4,940,730

DATED : July 10, 1990

INVENTOR(S) : K. Wakamatsu, et al.

It is certified that error appears in the above-identified patent and that said Letters Patent is hereby corrected as shown below:

Claim 1, line 1, delete "[The]"
Claim 1, lines 1-2, delete "[according to claim 10, wherein]"
Claim 1, line 3, delete "[is]"
Claim 1, line 4, delete "[.]"

Claim 2, line 1, delete "[The]"
Claim 2, lines 1-2, delete "[according to claim 10, wherein]"
Claim 2, line 3, delete "[is]"
Claim 2, line 4, delete "[.]"

Signed and Sealed this

Seventeenth Day of September, 1991

Attest:

HARRY F. MANBECK, JR.

*Attesting Officer*      *Commissioner of Patents and Trademarks*